United States Patent
Filippo

(10) Patent No.: US 10,328,644 B2
(45) Date of Patent: Jun. 25, 2019

(54) METHOD FOR INTRODUCING AN ACTIVE COMPOUND INTO A SOFT HYDRATED CONTACT LENS

(71) Applicant: SAFILENS S.R.L., Staranzano (GO) (IT)

(72) Inventor: Alessandro Filippo, Azzano Decimo (IT)

(73) Assignee: SAFILENS S.R.L., Staranzano (GO) (IT)

( * ) Notice: Subject to any disclaimer, the term of this patent is extended or adjusted under 35 U.S.C. 154(b) by 39 days.

(21) Appl. No.: 15/300,201

(22) PCT Filed: Mar. 27, 2015

(86) PCT No.: PCT/EP2015/056729
§ 371 (c)(1),
(2) Date: Sep. 28, 2016

(87) PCT Pub. No.: WO2015/150262
PCT Pub. Date: Oct. 8, 2015

(65) Prior Publication Data
US 2017/0151734 A1    Jun. 1, 2017

(30) Foreign Application Priority Data

Apr. 1, 2014   (IT) .............. PD2014A0083

(51) Int. Cl.
| | | |
|---|---|---|
| *B29D 11/00* | (2006.01) | |
| *A61L 12/02* | (2006.01) | |
| *A61K 31/728* | (2006.01) | |
| *A61K 31/716* | (2006.01) | |
| *G02C 13/00* | (2006.01) | |
| *A61K 9/00* | (2006.01) | |
| *A61K 31/726* | (2006.01) | |
| *A45C 11/00* | (2006.01) | |
| *A61L 12/14* | (2006.01) | |
| *B29K 633/04* | (2006.01) | |
| *B29K 683/00* | (2006.01) | |

(52) U.S. Cl.
CPC ...... *B29D 11/00096* (2013.01); *A45C 11/005* (2013.01); *A61K 9/0051* (2013.01); *A61K 31/726* (2013.01); *A61K 31/728* (2013.01); *A61L 12/02* (2013.01); *A61L 12/14* (2013.01); *A61L 12/142* (2013.01); *B29D 11/00067* (2013.01); *B29K 2633/04* (2013.01); *B29K 2683/00* (2013.01)

(58) Field of Classification Search
CPC ... A61L 12/026; A61K 31/728; A61K 31/716; B29D 11/00096; G02C 13/008
See application file for complete search history.

(56) References Cited

U.S. PATENT DOCUMENTS

| | | | | |
|---|---|---|---|---|
| 3,050,422 A | | 8/1962 | Zak | |
| 3,973,760 A | * | 8/1976 | Browning | A61L 2/025 366/111 |
| 4,382,824 A | * | 5/1983 | Halleck | A61L 2/02 134/1 |
| 4,697,605 A | * | 10/1987 | Yung | A61L 2/025 134/107 |
| 5,129,410 A | * | 7/1992 | Ifejika | G02C 13/008 134/1 |
| 5,431,879 A | * | 7/1995 | Heyl | A45C 11/005 134/901 |
| 6,183,705 B1 | * | 2/2001 | Chang | A61L 12/026 134/901 |
| 6,193,806 B1 | * | 2/2001 | Reed | A45C 11/005 134/1 |
| 2008/0190447 A1 | * | 8/2008 | Simonette | A61L 12/026 134/1 |
| 2010/0240776 A1 | * | 9/2010 | Filippo | A61L 12/04 514/781 |
| 2013/0152978 A1 | | 6/2013 | Allred et al. | |

FOREIGN PATENT DOCUMENTS

| | | |
|---|---|---|
| EP | 1861069 A1 | 12/2007 |
| EP | 2526974 A1 | 11/2012 |
| WO | 9913863 A1 | 3/1999 |
| WO | 2006085351 A1 | 8/2006 |

OTHER PUBLICATIONS

Karkkainen, T. R., M. K. Smith, and J. R. Wood. "The Effect Contact Lens Solution Osmolarity Has on Tear Film Tonicity." Investigative Ophthalmology & Visual Science 43.13 (2002): 3090-3090.*

* cited by examiner

*Primary Examiner* — Bethany P Barham
*Assistant Examiner* — Peter Anthopolos
(74) *Attorney, Agent, or Firm* — Volpe and Koenig, P.C.

(57) ABSTRACT

A method for introducing an active compound into a soft hydrated contact lens comprising the steps of: providing a hypotonic aqueous solution having an osmolarity value less than 150 mOsm and an effective quantity of that active compound, immersing the soft contact lens in the aqueous hypotonic solution, subjecting the contact lens immersed in the aqueous hypotonic solution to mechanical vibrations having a power greater than 100 mW for a predetermined time.

10 Claims, 1 Drawing Sheet

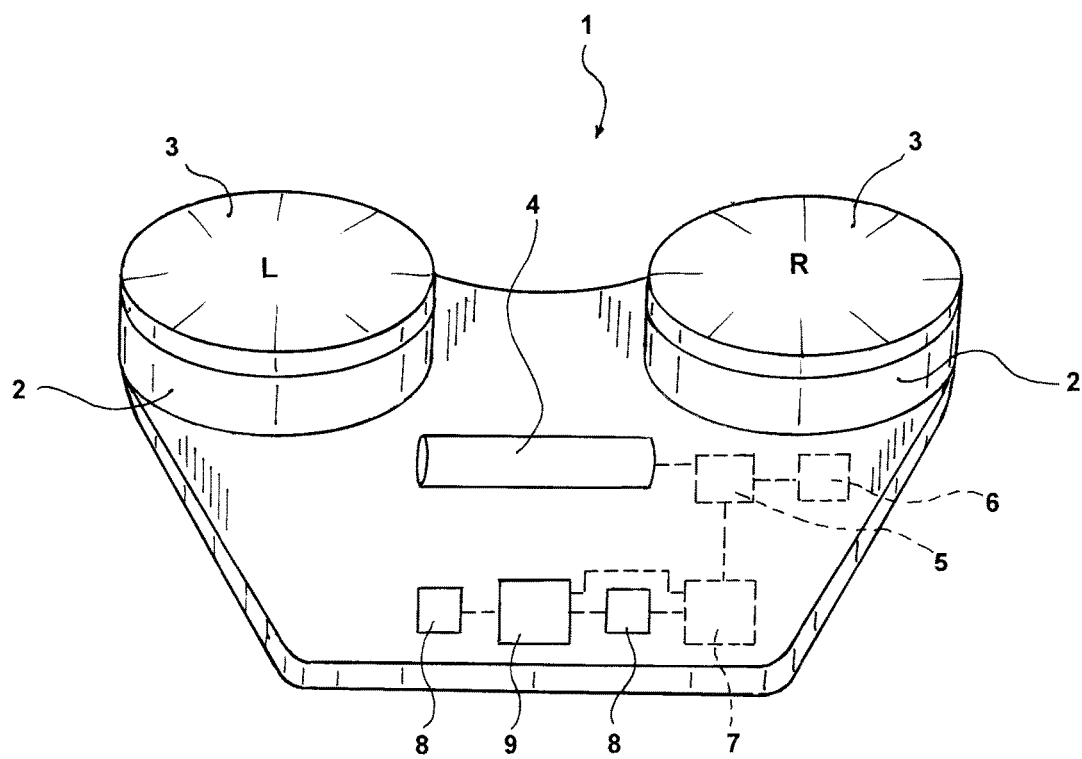

METHOD FOR INTRODUCING AN ACTIVE COMPOUND INTO A SOFT HYDRATED CONTACT LENS

TECHNICAL FIELD

The present invention relates to a method for treating soft contact lenses, in particular for introducing an active compound into a soft hydrated contact lens.

The invention further relates to the use of an aqueous hypotonic solution as a preserving solution for soft contact lenses, and to a kit comprising a container device for soft contact lenses and a preserving solution for the contact lenses.

BACKGROUND ART

The use of contact lenses among the population is very widespread. In particular, there are known so-called "soft" contact lenses which, with respect to the other types of contact lens (rigid or semi-rigid), afford a greater level of comfort when worn by the user.

This advantageous characteristic is provided by the high hydrophilic capacities of the polymer materials of which the contact lenses are realized. Such polymer materials, being capable of retaining a relevant quantity of water, allows greater compatibility between the lens and eye, as well as a greater deformability of the lens which allows it to better adapt to the surface of the eye.

More specifically, soft contact lenses may be constructed from polymers which have a large number of hydrophilic functional groups, for example, hydroxyls, which are capable of forming weak dipolar bonds (hydrogen bonds) with the water molecules. As a result of these characteristics, soft contact lens can contain a proportion of water by weight of from 25% to 75% with respect to the total weight of the contact lens, forming a hydrogel in which a solid matrix, which defines the structural portion of the lens and is constituted by the polymer material, is immersed in a liquid component which is uniformly distributed in the solid matrix.

Known examples of polymer materials used in the construction of the solid component of soft contact lenses are constituted by HEMA-based polymers (hydroxyethyl methacrylate) or by silicone polymers.

In addition, the liquid component is typically formed by an aqueous solution of sodium chloride at 0.9% by weight, which is known as "physiological solution", which reproduces, at least in terms of the sodium chloride content, the composition of the natural lachrymal film which superficially covers the cornea of the eye. In this manner, the contact lens is more compatible with the surrounding ocular environment and the presence thereof on the surface of the eye is less irritating for the user.

In fact, it is known that one of the greatest disadvantages arising from the use of contact lenses, including soft contact lenses, is represented by the sensation of ocular dryness which is caused by the reduction or by the breaking of the lachrymal film. This fact typically involves a sensation of irritation and intolerance which often compels the user to take off the lenses and which, over time, may also result in changes to the lachrymal functionality and to other pathological dysfunctions causing detriment of the eye (such as, for example, inflammations at the cornea or conjunctiva).

In order to overcome, at least partially, this disadvantage, it is known to use external solutions which are administered in drops directly to the eye, to which the contact lens is applied.

Those external solutions may be formed by simple physiological solutions, as defined above, or, in a more effective version, by aqueous solutions which are generally and generically known as "lachrymal substitutes".

Those solutions have particular physical, chemical and rheological characteristics as well as biocompatibility characteristics which are capable of reproducing to the greatest possible extent the properties of the natural lachrymal fluid.

In particular, lachrymal substitutes have specific viscoelastic properties, in particular a prominent pseudo-plastic behaviour (with viscosity of the solution which decreases with an increase of the shear stress applied), as well as hydrophilic, muco-adhesive (in order to remain attached for the longest possible time to the mucinase component of the lachrymal film), mucomimetic (in order to simulate in the best manner possible the behaviour of the lachrymal film) and wettability properties, in addition, naturally, to general compatibility with the tissues of the eye.

Those particular properties are conferred on lachrymal substitutes by specific compounds, generally polymers, such as polysaccharides, polyvinyl alcohols, derivatives of cellulose, having a molecular weight which is relatively high, in the order of hundreds of thousands Dalton.

However, the beneficial action of those external solutions is limited over time, so that it may be necessary to carry out those operations several times per day, which operation is inconvenient and very unwelcome to the users.

A second technical solution to the problem mentioned above which is described in EP1861069, in the name of the Applicant, provides for the production of a soft contact lens in which a lachrymal substitute is incorporated therein.

In that case, the liquid component of the contact lens is not formed by a simple physiological solution but, instead, by a lachrymal substitute as defined above. This type of contact lens is obtained by immersing a dry semifinished product, which does not have any water at the inner side thereof and which is formed by the solid component of the contact lens, in an aqueous solution which also contains, in addition to 0.9% sodium chloride, an effective quantity, typically from 0.1% to 0.3% by weight, of an active compound which is capable of conferring on the solution adequate viscoelastic characteristics in addition to muco-adhesive and mucomimetic properties. In particular, that compound is preferably hyaluronic acid or a sodium salt thereof, or a galactoxyloglucan which is extracted from tamarind seeds (TSP), those polymers conferring on the aqueous solution the properties required in terms of muco-adhesion, muco-mimetic nature and pseudo-plasticity.

The contact lenses produced according to EP1861069, once they are applied to the eye, release a fraction of the lachrymal substitute contained therein, substantially improving the sensation of comfort of the user.

In this manner, however, the content of active compound which characterizes the liquid component of the contact lens, so as to allow the definition thereof as a lachrymal substitute, progressively tends to decrease, so that the contact lens, application after application, becomes less and less comfortable.

That loss over time of the excellent initial performance levels in terms of comfort, suggests the provision for contact lenses of this type of relatively frequent replacement, for example, weekly replacement or, even better, daily replacement.

In order to counteract the phenomenon of the loss of active compound of the liquid component of the contact lens in successive applications, EP1861069 suggests the use of a preserving solution, defined as a solution which is suitable for conserving the soft contact lenses between an application to the eye and the subsequent application (also known as "care solutions"), which is formed by physiological solution supplemented, in addition to a disinfectant agent, by an effective quantity of the active compound already present in the soft contact lens, for example, hyaluronic acid or TSP. In this manner, a fraction of active compound is absorbed in the external superficial layers of the contact lens, partially restoring the quantity of active compound previously released in the eye.

The efficacy of that expedient, however, is greatly limited by the fact that the absorption of the active compound within the contact lens is opposed by the difficulty which the polymers with a high molecular weight have in being introduced inside the lens, in particular when the lens is a lens which is already hydrated. In fact, the mean diameters of the pores of the solid component of the lens are in the order of magnitude of the molecules of active compound, so that the mere exchange by diffusion determined by the difference in concentration of active compound between the external solution with respect to the contact lens and the liquid component present inside the lens is generally insufficient to diffuse the polymer in a substantially uniform manner inside the contact lens.

Consequently, therefore, as anticipated above, the active compound is absorbed only at the external superficial layers of the lens, without extending into deep, in this manner preventing the introduction into the lens of additional polymer and therefore limiting the quantity of active compound incorporated in the contact lens.

In different application fields, it is further known to use a soft contact lens acting as a therapeutic carrier, in particular as a device which is capable of slowly releasing over time one or more medicaments at the surface of the eye. In this case, the aqueous solution comprising the medicament to be released in the eye is introduced in the body of the contact lens during the production step of the lens (at the reticulation step of the polymer which forms the body of the lens or also at the hydration step of the lens).

In that case, the simple immersion of the lens in an aqueous solution comprising the medicament is also not sufficiently effective to restore the medicament which is released by the contact lens in the eye.

Therefore, there exists a need to provide a method which allows the effective introduction into hydrated soft contact lenses of an active compound, in particular an active compound which is selected from a lubricating agent and a medicament to be released in a controlled manner inside the eye.

DISCLOSURE OF THE INVENTION

The problem addressed by the present invention is to provide a method for introducing an active compound into a soft hydrated contact lens, which method is functionally configured to comply with the needs and to overcome the limitations set out above with reference to the cited prior art.

Within the scope of that problem, a main object of the invention is to provide a method which allows an effective introduction into a soft hydrated contact lens of an active compound which is formed by molecules having a high molecular weight greater than 100 KDalton.

Another object of the invention is to provide a method which allows the restoration of an active compound in hydrated soft contact lenses, wherein that active compound is already present in the liquid component of the lens, between one application and the next of the contact lens to the eye of a user, in such a manner that the beneficial effects of the release in the eye of the active compound are extended over time.

That problem is solved and those objects are achieved by the present invention by means of a method carried out in accordance with the appended claims.

In a first aspect thereof, the present invention relates to a method for introducing an active compound into a soft hydrated contact lens, wherein there are provided the steps of:

providing a hypotonic aqueous solution which has an osmolarity value less than 150 mOsm and in which an effective quantity of the active compound is dissolved, immersing the soft contact lens in the aqueous hypotonic solution, and subjecting the contact lens immersed in the aqueous hypotonic solution to mechanical vibrations having a power greater than 100 mW for a predetermined time.

By means of this method, the Applicant has surprisingly found that the quantity of active compound incorporated within a soft contact lens is significantly greater than the quantity of active compound introduced into the lens by means of simple immersion of the contact lens in a substantially isotonic aqueous solution comprising the active compound and without any application of vibrations.

In fact, the Applicant has discovered and verified that the mechanical vibrations, under some conditions, may promote the introduction of an active compound, even one of high molecular weight, within the soft contact lens.

In particular, the Applicant has carried out various tests, immersing soft hydrated contact lenses in aqueous solutions having the same concentration of an active compound but a different osmolarity (obtained by varying the fraction by weight in a sodium chloride solution) and then subjecting some of those contact lenses immersed in the aqueous solutions to mechanical vibrations.

In fact, the tests have demonstrated that:
a) the contact lenses immersed in aqueous solutions having low osmolarity incorporate more active compound with respect to contact lenses immersed in solutions having high osmolarity,
b) the contact lenses immersed in aqueous solutions having low osmolarity incorporate more active compound when they are subjected to mechanical vibrations with respect to the same contact lenses which are not subjected to mechanical vibrations and
c) the contact lenses immersed in aqueous solutions having high osmolarity incorporate a small relevant quantity of active compound both when they are subjected to mechanical vibrations and when they are not.

The first result set out above demonstrates how the hypotonic solution tends to be introduced inside the soft contact lens even if it is already hydrated, appearing with a behaviour which is similar to the phenomenon of osmosis, as if the contact lens were a semi-permeable membrane which separates the external solution from the internal liquid component thereof. This leads to a swelling of the soft contact lens when it is immersed in a hypotonic aqueous solution which, during introduction into the lens, also carries with it, at least partially, the active compound dissolved therein.

However, the active compound is able to enter the contact lens if it has sufficiently small dimensions to be able to be introduced inside the pores of the contact lens.

Preferably, the active compound is selected from a lubricating agent and a medicament.

In the field of lubricating agents, the above characteristic becomes particularly important because those agents are often formed by molecules having a high molecular weight, in the order of hundreds of thousands Dalton, in particular those which are more suitable for conferring on an aqueous solution the viscoelastic, muco-adhesive and mucomimetic properties which are required for a lachrymal substitute, such as hyaluronic acid (or a salt thereof) and TSP, which preferably have molecular weight values of from 600 to 1000 KDa.

As regards the second aspect mentioned above, the Applicant has surprisingly discovered that the mechanical vibrations applied to the contact lens which is immersed in the aqueous solution which contains the active compound may have a positive influence in favour of the introduction thereof into the contact lens and, furthermore, that this positive influence is correlated with the degree of osmolarity of the aqueous solution.

The results of the tests show how the effect of the mechanical vibrations in favour of the introduction of an active compound inside a contact lens which is immersed in an aqueous solution is substantial when that solution has an osmolarity less than approximately 150 Osm.

It is further preferable for the mechanical vibrations to have a power of at least 100 mW. In a greatly preferred manner, the mechanical vibrations have a power of approximately from 150 to 200 mW.

Without being bound by a scientific theory, the Applicant considers that the positive effect brought about by the mechanical vibrations on the contact lens/aqueous solution system may be attributable to the combination of the following phenomena:

the effect of greater dispersion in water obtained in respect of the mechanical vibrations on the active compounds, and the effect of recirculating the water bonded inside the hydrogel which forms the contact lens.

In the first case, the tests carried out by the Applicant have demonstrated that the mechanical vibrations break up any possible agglomerations of molecules of active compound which are present in the solution, in particular polymers having a high molecular weight, so as to reduce the mean dimension thereof and to promote the passage thereof through the pores of the contact lens.

The second phenomenon results from considerations relating to the fact that a portion of the water which forms the internal liquid component of the contact lens is bonded by means of weak dipolar bonds to the hydrophilic groups of the polymer which forms the hydrogel of the contact lens. The mechanical vibrations may provide the quantity of energy necessary for breaking those dipolar bonds and for bringing about the recirculation of the water molecules between the inner side and the outer side of the contact lens, thereby consequently also promoting the introduction into the contact lens of the active compound which is dissolved in the external water with respect to the lens.

A high tonicity of the aqueous solution resulting in a high presence of sodium chloride ions appears to impede one and/or other of the above-mentioned phenomena, preventing the beneficial effects of the mechanical vibrations.

The soft contact lenses which are subjected to the process of introducing an active compound in accordance with the present invention may be manufactured with any known method and, preferably, they are formed by a hydrogel, whose solid component is composed by a polymer matrix based on HEMA or based on silicone, properly hydrated.

The liquid component of the contact lens may be formed by a physiological solution (aqueous solution with 0.9% sodium chloride) or by other aqueous solutions which are used in the production of soft contact lenses.

Preferably, the introduction of the active compound in the soft contact lens is carried out between successive applications of the soft contact lens to an eye of a user.

In a preferred embodiment, the liquid component of the soft contact lens already comprises the active compound present in the hypotonic aqueous solution and the introduction of the active compound into the contact lens by means of the method of the invention serves to restore the quantity of active compound released in the eye by the soft contact lens.

Therefore, the hypotonic aqueous solution is preferably a preserving solution for soft contact lenses and comprises a disinfecting agent in order to disinfect the soft contact lens when it is immersed therein. In that manner, the active compound is advantageously introduced into the soft contact lens after a first application, in which a portion of the active compound present in the lens has been released into the eye, and before a successive application, in which the lens is repositioned on the eye.

The present hypotonic aqueous solution may comprise, as a disinfecting agent, any compound which is normally used in the common preserving solutions of soft contact lenses, for example, ethylenediaminetetraacetic acid (EDTA) or polyhexamethylene biguanide (PHMB).

In a preferred version, the hypotonic aqueous solution may further have an osmolarity less than 130 mOsm.

In this manner, there is further increased both the swelling effect of the contact lens with the aqueous solution with a resultant greater introduction of the active compound dissolved therein, and the positive effect brought about by the mechanical vibrations on the solution/contact lens system.

In another preferred version, the hypotonic aqueous solution has an osmolarity greater than 100 mOsm in such a manner that the contact lens at the end of the processing operation to which the present invention relates does not have an excessively low tonicity level.

In fact, this could also cause an initial sense of irritation for the user at the time of application of the contact lens to the eye.

The tonicity of the aqueous solution is preferably adjusted by the presence of sodium chloride which, together with the other components dissolved therein, in particular the active compound, forms the total tonicity of the solution.

In a preferred version of the invention, the hypotonic aqueous solution comprises a fraction by weight of NaCl less than 0.4%.

In another preferred form, the hypotonic aqueous solution comprises a fraction by weight of NaCl higher than 0.2%.

In a very preferred manner, the hypotonic aqueous solution comprises a fraction by weight of NaCl of approximately 0.3%.

In a first embodiment of the invention, the active compound comprises a lubricating agent which is selected from hyaluronic acid or a derivative thereof, in particular a salt thereof, galactoxyloglucan extracted from tamarind seeds (TSP) and an admixture thereof.

Preferably, the hyaluronic acid or a salt thereof and the TSP have a mean molecular weight which makes them suitable, in a proper concentration, for making an aqueous solution a lachrymal substitute.

In particular, the hyaluronic acid or a salt thereof and the TSP have a mean molecular weight between 600 and 1000 KDa, preferably approximately 800 KDa.

The fraction by weight of hyaluronic acid or a salt thereof in the hypotonic aqueous solution is preferably less than 0.05%.

In fact, the Applicant has noted that the presence of a greater quantity of this compound in a hypotonic aqueous solution may reduce the action of the disinfecting agent which may be present, removing from the solution a necessary characteristic for the use thereof as a preserving solution.

In a preferred embodiment, the lubricating agent comprises an admixture of hyaluronic acid or a salt thereof and TSP.

In fact, this last compound has good bacteriostatic properties so that the presence thereof in a preserving solution allows the achievement of adequate levels of concentration of lubricating agent without an excess of hyaluronic acid which, as mentioned above, would cause a reduction in the disinfecting capacities thereof.

The hypotonic aqueous solution preferably comprises a fraction by weight of hyaluronic acid or a salt thereof which is not less than approximately 0.01% and a fraction by weight of TSP which is not less than approximately 0.005%.

In a first preferred embodiment, the hypotonic aqueous solution comprises a fraction by weight of hyaluronic acid or a salt thereof of approximately 0.015% and a fraction by weight of TSP of approximately 0.015%.

In a second preferred embodiment, the hypotonic aqueous solution comprises a fraction by weight of hyaluronic acid or a salt thereof of approximately 0.035% and a fraction by weight of TSP of approximately 0.035%.

In a further embodiment of the invention, the active compound dissolved in the hypotonic aqueous solution comprises a medicament.

The medicament may be any compound which is used as an active ingredient for treating a pathology of the user to be administered by the application of a soft contact lens to the eye.

In particular, the medicament may be a compound which is used as an active ingredient for treating a pathology of the eye.

Examples of medicaments which may be used as active compounds in accordance with the present invention are:

antibiotic agents such as fluoroquinolones (for example, ofloxacin) or the amino glycosides (for example, tobramicin);

hypotonic agents which are capable of reducing the intraocular pressure, such as timolol maleate, brimonidine, carteolol hydrochloride, or similar agents of prostaglandin (for example, bimatoprost);

anti-inflammatory agents such as cortico-steroids (for example, desametasone, fluorometholone or loteprednol etabonate);

anti-allergic agents such as anti-histamines (for example, chlorphenamine) or sodium cromoglicate or lodoxamide.

The mechanical vibrations to which the soft contact lens which is immersed in the hypotonic solution is subjected preferably have a frequency of at least 100 Hz and, more preferably, a frequency of between 150 and 250 Hz.

The contact lens which is immersed in the hypotonic aqueous solution set out above is subjected to mechanical vibrations for a sufficient time to allow the introduction of a desired quantity of active compound.

That period of time is at least 10 seconds and, preferably, is between 1 and 3 minutes.

In a preferred form, the contact lens which is immersed in the hypotonic aqueous solution is subjected to mechanical vibrations for successive cycles of from 2 to 10 seconds every 10 to 25 minutes.

In a second aspect thereof, the invention relates to the use of a hypotonic aqueous solution having an osmolarity value less than 150 mOsm, comprising a disinfecting agent and an effective quantity of an active compound, as preserving solutions for soft contact lenses.

In a third aspect thereof, the invention relates to a kit comprising a preserving solution for soft contact lenses including an aqueous hypotonic solution having an osmolarity value less than 150 mOsm, a disinfecting agent and an effective quantity of an active compound, as well as a container device for at least one soft contact lens including a receptacle which is provided for receiving the contact lens so as to be immersed in the above-mentioned aqueous hypotonic solution and a vibrating member which is associated with the receptacle for subjecting the soft contact lens and the aqueous hypotonic solution in which it is immersed to mechanical vibrations having a power of at least 100 mW.

Preferably, in each of the second and third aspects, the hypotonic aqueous solution has one or more of the characteristics set out above, in particular in relation to the tonicity thereof, the content of active compound, disinfecting agent and sodium chloride.

Furthermore, the container device preferably has such dimensions and is programmed so that the vibrating member generates mechanical vibrations having the properties set out above, in particular in terms of frequency, power and duration.

BRIEF DESCRIPTION OF THE DRAWINGS

The features and advantages of the invention will be better appreciated from the detailed description of a preferred embodiment thereof which is illustrated by way of non-limiting example with reference to the single appended drawing, in which FIG. 1 is a schematic perspective view of a device for containing a contact lens which is provided for operating in accordance with the method of the present invention.

PREFERRED EMBODIMENT OF THE INVENTION

In the appended single FIGURE, there is generally designated 1 a device for containing a contact lens which is provided to operate in accordance with the method for introducing an active compound into a contact lens of the present invention.

The device 1 comprises a pair of receptacles 2, for example of cup-like form, each receptacle 2 being provided to contain a contact lens which is immersed in a preserving solution and being able to be closed with a cap 3.

The device 1 further comprises a vibrating member 4 which is associated with the pair of receptacles 2 in order to subject the receptacles and the content thereof to mechanical vibrations.

More specifically, the vibrating member 4 may be of the type having an eccentric mass which is caused to rotate about an axis thereof at a predefined rate by an electric motor 5 which is supplied, for example, by a battery 6.

The activation and deactivation of the electric motor 5 is controlled by a control unit 7 which is inside the device 1, preferably of the programmable type, which can be activated by the user by means of buttons 8.

A display 9 which is connected to the control unit 7 communicates to the user information concerning the operating state of the device 1.

In the preferred version described here, the electric motor 5 has a maximum input power of approximately 300 mW and actuates the vibrating member 4 in such a manner as to generate mechanical vibrations at a frequency between 150 and 250 Hz, preferably approximately 200 Hz.

The control unit 7 may be programmed in order to carry out a cycle of vibrations for a predetermined time or, in a greatly preferred manner, to carry out successive cycles of generation of vibrations alternating with rest periods.

The device 1 is advantageously used as a container for placing the soft contact lenses at the end of the day (or the period of application to the eye) in a state immersed in a preserving solution having the characteristics set out above in the general description of the invention.

A preferred example of preserving solution, in which the soft contact lens is immersed, is a solution of distilled water in which the following components are dissolved:

hyaluronic acid (MW of approximately 800 KDa): 0.015%

TSP (MW of approximately 800 KDa): 0.015% boric acid: 0.43% disodium tetraborate: 0.085% sodium chloride: 0.3%

EDTA: 0.1% polyquaternium-2: 0.001% viscosity promoters: 1% polyhexamethylene biguanide solution: 0.0005%

The solution has an osmolarity value of approximately 125 mOsm.

Once the control unit 7 has been activated by means of the buttons 8, the vibrating member 4 is actuated by the motor 5 for a first period of time of approximately 15 seconds, after which it begins a series of cycles of switching on and off in which the switching off period lasts approximately 15 minutes and the switching on period lasts approximately 5 seconds, which continue in succession in such a manner that the total period of actuation of the vibrating member 4 is approximately 2 minutes.

The soft contact lens immersed in the preserving solution absorbs a given quantity of solution which is estimated at approximately 20 microliters, while the action of the mechanical vibrations, breaking up any agglomerations of active compound and/or causing the dynamic recirculation of the water bonded to the hydrogel internally with respect to the contact lens, also promotes the introduction of the active compound therein so as to obtain a substantial equilibrium between the concentration of active compound in the liquid component inside the contact lens and in the preserving solution outside it.

The soft contact lens taken from the receptacle 2 at the end of the processing operation has therefore incorporated in its own liquid component a significant quantity of active compound and may be applied to the eye of the user again.

The present invention therefore solves the problem set out above with reference to the cited prior art.

The invention claimed is:

1. A method for introducing a lubricating agent into a soft hydrated contact lens, the method comprising:
   providing a hypotonic aqueous solution having an osmolarity value less than 150 mOsm and comprising an effective quantity of the lubricating agent to be introduced into the contact lens,
   immersing the soft contact lens in the aqueous hypotonic solution,
   subjecting the contact lens immersed in the aqueous hypotonic solution to mechanical vibrations having a power greater than 100 mW for a predetermined time, wherein the predetermined time during which the contact lens, immersed in the aqueous hypotonic solution, is subjected to mechanical vibrations, is at least 10 seconds, divided into cycles of 2 to 10 seconds every 10 to 25 minutes.

2. The method according to claim 1, wherein the lubricating agent is introduced between applications of the soft contact lens to an eye of a user.

3. The method according to claim 1, wherein the aqueous hypotonic solution further comprises a disinfecting agent in order to disinfect the soft contact lens when it is immersed therein.

4. The method according to claim 1, wherein the mechanical vibrations have a frequency of at least 100 Hz.

5. The method according to claim 1, wherein the aqueous hypotonic solution has an osmolarity of from 100 mOsm to 130 mOsm.

6. The method according to claim 1, wherein the aqueous hypotonic solution comprises a fraction by weight of NaCl of from 0.2% to 0.4%.

7. The method according to claim 1, wherein the lubricating agent is selected from the group consisting of: hyaluronic acid, a salt thereof, galactoxyloglucan extracted from tamarind seeds and an admixture thereof.

8. The method according to claim 7, wherein (1) the lubricating agent is the admixture of (i) hyaluronic acid or a salt thereof and (ii) the galactoxyloglucan extracted from tamarind seeds, and (2) the hyaluronic acid or salt thereof is present at a fraction by weight of less than 0.05% of the hypotonic aqueous solution.

9. The method according to claim 8, wherein the hyaluronic acid or a salt thereof is present in the aqueous hypotonic solution at a fraction by weight of from 0.01% to 0.035% and the galactoxyloglucan extracted from tamarind seeds is present in the aqueous hypotonic solution at a fraction by weight of from 0.005% to 0.035%.

10. The method according to claim 1, wherein the soft hydrated contact lens comprises a hydrogel based on hydroxyethyl methacrylate or based on silicone.

\* \* \* \* \*